United States Patent [19]

Meyer

[11] 4,363,142
[45] Dec. 14, 1982

[54] PROSTHETIC HEART VALVE

[75] Inventor: Louis C. Meyer, Denver, Colo.

[73] Assignee: Mitral Medical, Inc., Wheat Ridge, Colo.

[21] Appl. No.: 84,318

[22] Filed: Oct. 12, 1979

[51] Int. Cl.³ ............................................. A61F 1/22
[52] U.S. Cl. .................................. 3/1.5; 137/512.1; 137/527.8
[58] Field of Search ................... 3/1.5; 137/512.1, 527, 137/527.8

[56] References Cited

U.S. PATENT DOCUMENTS

| 3,312,237 | 4/1967 | Mon et al. | 3/1.5 X |
| 3,370,305 | 2/1968 | Goott et al. | 3/1.5 |
| 3,416,563 | 12/1968 | Lee | 3/1.5 |
| 3,445,863 | 5/1969 | Wada | 3/1.5 |
| 3,538,514 | 11/1970 | Schimert et al. | 3/1.5 |
| 3,589,392 | 6/1971 | Meyer | 3/1.5 X |
| 3,835,475 | 9/1974 | Child | 3/1.5 |
| 3,903,548 | 9/1975 | Nakib | 3/1.5 |
| 3,959,827 | 6/1976 | Kaster | 3/1.5 |
| 4,011,601 | 3/1977 | Clune et al. | 3/1.5 |
| 4,159,543 | 7/1979 | Carpentier | 3/1.5 |
| 4,178,639 | 12/1979 | Bokros | 3/1.5 |
| 4,254,508 | 3/1981 | Bokros | 3/1.5 |
| 4,272,854 | 6/1981 | Bokros | 3/1.5 |
| 4,276,658 | 7/1981 | Hanson et al. | 3/1.5 |

FOREIGN PATENT DOCUMENTS 2846299  5/1979  Fed. Rep. of Germany ........... 3/1.5

*Primary Examiner*—Clifford D. Crowder
*Attorney, Agent, or Firm*—John E. Reilly

[57] ABSTRACT

A prosthetic heart valve of the bileaflet type is characterized in particular by having leaflets in confronting relation to one another which are guided along opposite sides of the leaflets for accurate controlled swinging movement between open and closed positions in such a way that the guiding portions do not interfere with or restrict in any way the opening size of the valve but permit effective washing action as the blood flows therethrough.

17 Claims, 15 Drawing Figures

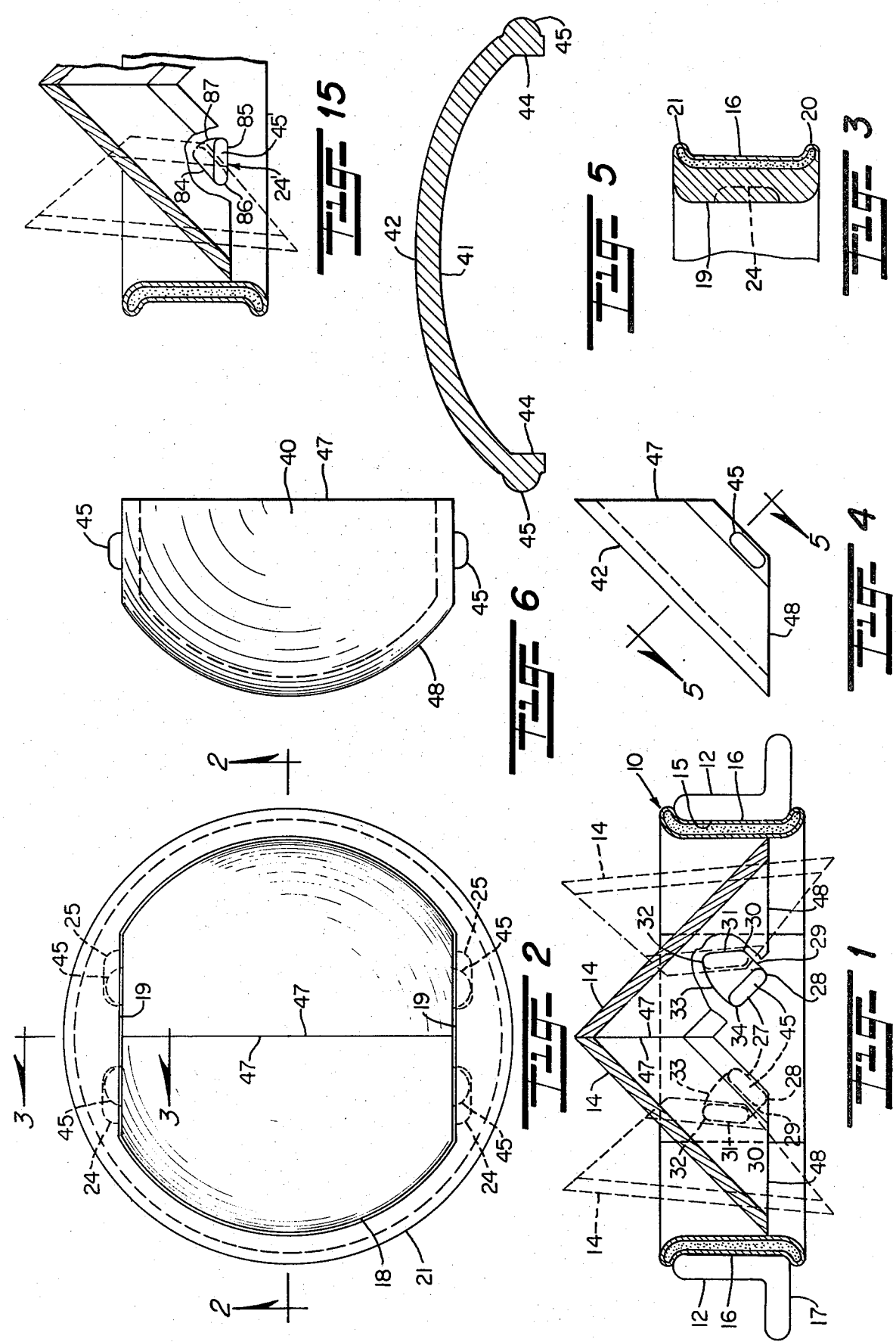

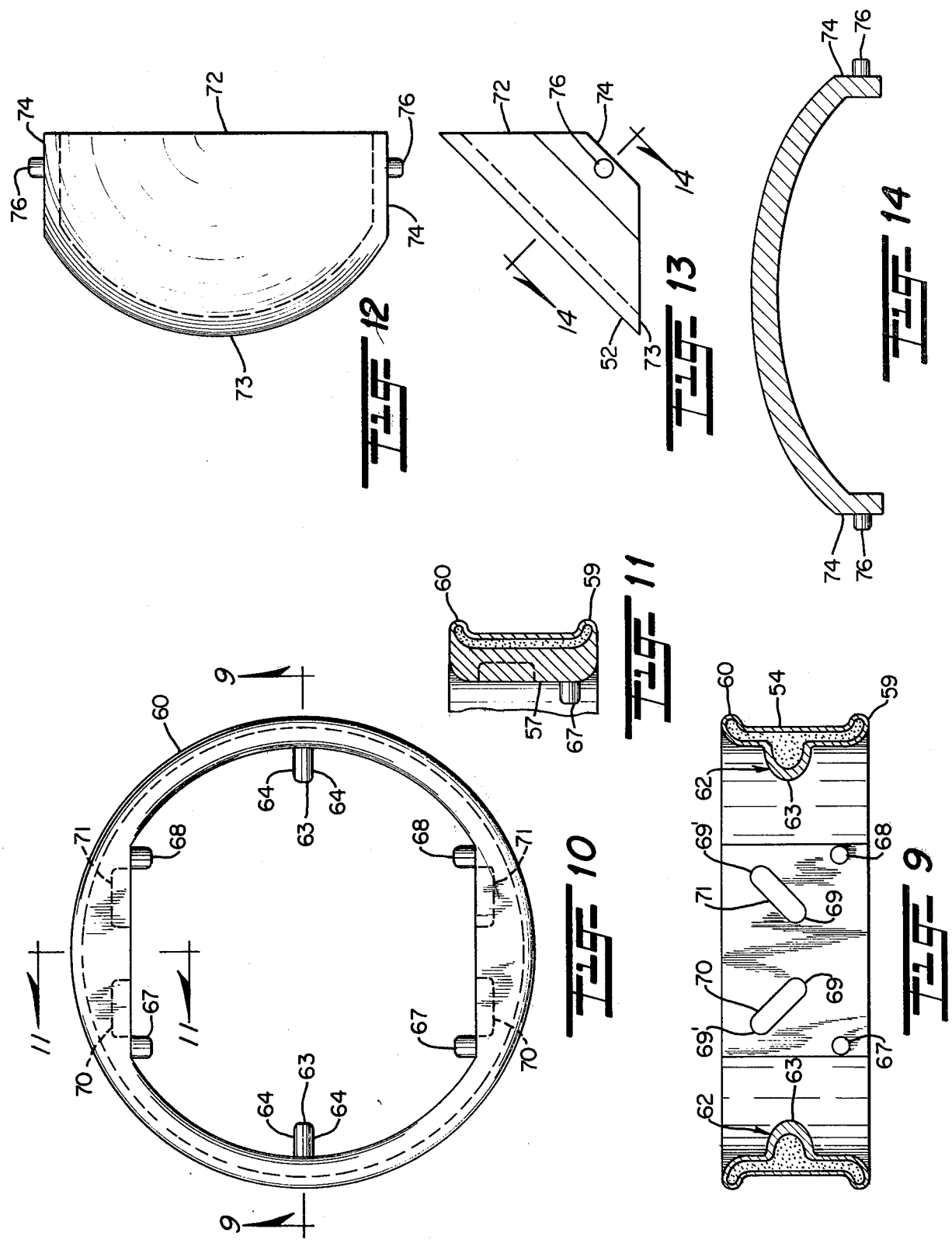

PROSTHETIC HEART VALVE

This invention relates to valves and more particularly relates to check valves of the type which are specifically adapted for use as artificial or prosthetic heart valves.

FIELD OF THE INVENTION

Numerous different types of artificial heart valves have been devised to the end of replacing defective natural heart valves and to simulate as closely as possible the operation of the natural heart valve. Essentially, the mitral or aortic valve in the human heart takes the form of a check valve and is characterized in particular by its rapid response to reversal in direction of blood flow to move between its open and closed positions. A particular problem associated with the design and development of artificial heart valves has been to closely simulate the rapid response time achieved by the natural heart valve under repeated opening and closing. For example, it has been proposed in the past to employ split or curved leaflets which are hinged along a fixed point or line to the valve body so as to be hinged for swinging movement between a normally closed position and an open position, reference being made to my earlier U.S. Pat. No. 3,589,392, granted in 1971. Other leaflet type valves have since been devised in which the leaflets are mounted for pivotal or swinging movement about a fixed axis, such as, by the utilization of pins or notched elements and reference is made here to U.S. Pat. Nos. 3,626,518 and 3,312,237. Other approaches have been taken in the past however to avoid utilization of a fixed pivot or hinge axis by employing outer guide surfaces in the wall of the valve body so as to permit more effective washing action by the blood and minimize the danger of clotting, stress or wear at those points and for example reference is made to U.S. Pat. Nos. 4,011,601 and 3,903,548.

SUMMARY OF THE INVENTION

The present invention is broadly directed to a novel and improved form of split leaflet valve which obviates the need for fixed pivot or hinge axes while achieving rapid response time together with unrestricted fluid flow and effective washing of all parts of the valve by the blood or other liquid flowing therethrough.

It is therefore an object of the present invention to provide for a novel and improved check valve which incorporates one or more valving elements movable between an open and closed position in response to the direction of fluid flow which eliminates the need for a fixed hinge line or pivot point but avoids any objectionable floating or misalignment of the valving elements.

It is another object of the present invention to provide for a novel and improved prosthetic heart valve of the split leaflet type in which the leaflets are so mounted and disposed with respect to a valve body as to be closely controlled in opening and closing movement, and will permit unrestricted flow of blood therethrough in the open position coupled with complete washing of all parts of the valve elements.

A further object of the present invention is to provide for a novel and improved heart valve which is characterized by its long wear, durability and rapid response time under repeated use.

It is an additional object of the present invention to provide for a novel and improved prosthetic heart valve which is lightweight in construction, comprised of a minimum number of parts and will closely simulate the function of a natural heart valve in either the aortic or mitral positions.

In accordance with the present invention, there has been devised a unique guide assembly interposed between a valve body and one or more valve elements or leaflets to directionally control the opening and closing movement of the valve element in response to the direction of flow of liquid therethrough and in such a way that the valve elements are movable between an open position to afford maximum unrestricted flow through the opening in the valve body and a closed position inhibiting the valve against reverse flow. More particularly, in a preferred form of the present invention, a pair of occluder leaflets are disposed in confronting relation to one another within a hollow valve body, and guide means support opposite lateral edge surfaces of the leaflets for movement between an open position in which the leaflets are substantially parallel to one another within the body and a closed position in which the leaflets extend angularly across the body with their leading edges abutting one another so as to be substantially sealed with respect to one another and to the body. The guide means include lateral projections on opposed lateral edge surfaces which cooperate with guide channels formed in the inner wall surface of the body at a location relatively near the leading edge of a respective leaflet and away from its trailing edge, each channel extending angularly in the direction of flow away from the leaflet when in the closed position so as to guide the swinging or pivotal movement of each leaflet between the open and closed positions. The guide channels are in the form of open pockets of generally polygonal configuration and which cooperate with the guide means to support the leaflets within the valve body against axial displacement or shifting with respect to one another in advancing between the open and closed positions.

In the preferred form, the occluder leaflets are defined by a pair of curved leaflets having skirts and laterally projecting slide members on the skirts which are slidable and pivotal within the guide pockets as described. The external or convex surfaces of the leaflets rock about inwardly projecting lobes in moving between the open and closed positions, and the limit stops are positioned upstream of the leaflets so as to engage the trailing ends of the leaflets as they are advanced between the open and closed positions. As a result, the leaflet arrangement as described affords full unrestricted opening, while eliminating sockets or limited apertures in which blood might otherwise collect and further affords close alignment between the leaflets coupled with rapid response time in opening and closing.

In a modified form of the present invention, a pair of leaflets are disposed in confronting relation to one another with guide members on opposed lateral edges of the leaflets to slide through inclined guide lane channels on opposite sides of the leaflets as the leaflets rock about outer fulcrums in the wall of the valve body. The leaflets are formed with skirts or axial projections along opposite lateral edge surfaces, and limit stops in the wall of the valve body will maintain alignment and prevent any displacement or shifting of the leaflets in moving between the open and closed positions.

Other objects, advantages and features of the present invention will be readily apparent from the following detailed description of the preferred and modified embodiments taken in conjunction with the accompanying drawings, in which:

BRIEF DESCRIPTION OF THE DRAWINGS

FIG. 1 is a cross-sectional view of a preferred form of heart valve in accordance with the present invention;

FIG. 2 is a top plan view of the preferred form of heart valve in accordance with the present invention;

FIG. 3 is a cross-sectional view taken about lines 3—3 of FIG. 2;

FIG. 4 is a side view in elevation of one of the occluder leaflets employed in the preferred form of invention;

FIG. 5 is an enlarged cross-sectional view taken about lines 5—5 of FIG. 4; and

FIG. 6 is a top plan view of a preferred form of leaflet;

FIG. 9 is a cross-sectional view of the modified form of valve body;

FIG. 10 is a top plan view of the valve body shown in FIG. 9;

FIG. 11 is a cross-sectional view taken about lines 11—11 of FIG. 10;

FIG. 12 is a top plan view of one of the occluder leaflets of the modified form of invention;

FIG. 13 is a side view of one of the occluder leaflets of the modified form;

FIG. 14 is a cross-sectional view taken about lines 14—14 of FIG. 13; and

FIG. 15 is another view partially in section illustrating a modification in the guide members for the preferred form of invention as shown in FIG. 1.

DETAILED DESCRIPTION OF THE PREFERRED EMBODIMENT

Figure 8:
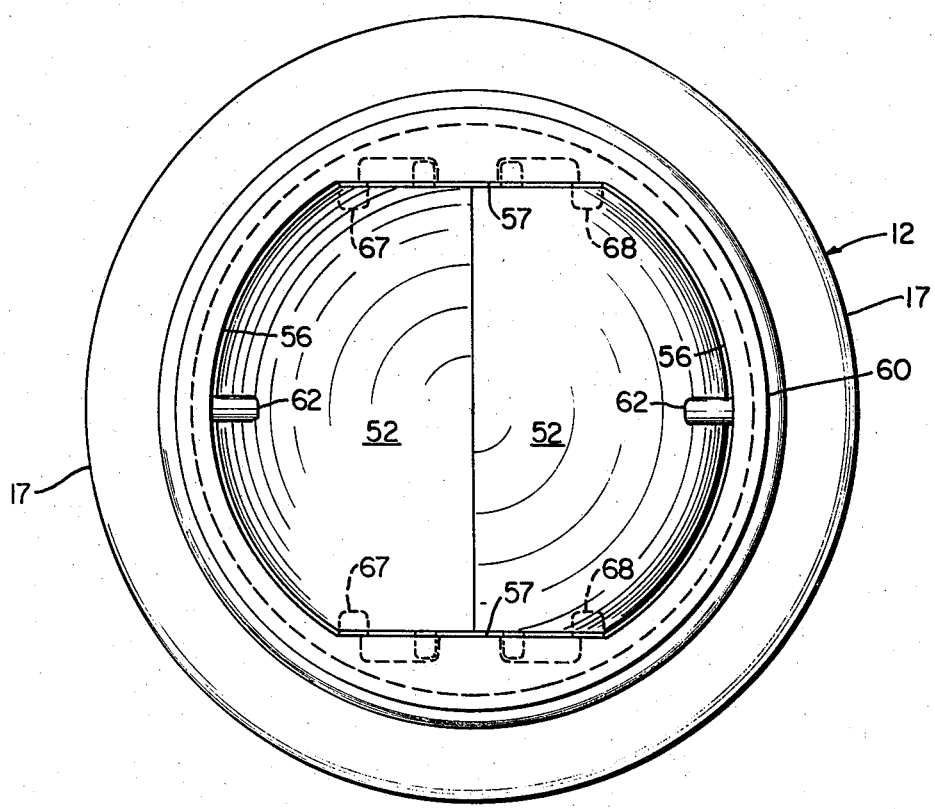
FIG. 8 is a top plan view of the modified form shown in FIG. 7.

As illustrated in FIGS. 1 to 6, the preferred embodiment of the present invention is broadly comprised of an annular valve body 10 surrounded by an outer concentric suture ring 12, the valve body containing a pair of occluder valve elements or leaflets 14. The outer suture ring 12 is of conventional construction and is shown more as a setting for the present invention in order to facilitate implantation of the valve in the heart, for example, in substitution for the mitral valve; or with slight modification is adapted to be positioned or substituted in place of the aortic valve. Broadly, the suture ring 12 includes an axially directed, circular wall portion 15 in outer concentric relation to the valve body, the wall portion 15 being of an axial length to fit snugly within the generally channel-shaped area of the external circular wall surface 16 of the valve body 10. A collar 17 projects radially and outwardly from one end of the ring of the upstream side of the valve for proper positioning of the entire assembly in place.

The valve body 10 is provided with diametrically opposed inner circular wall surfaces 18 in inner spaced concentric relation to the external wall surface 16, and the wall surfaces 16 and 18 terminate in radially and outwardly flared ends 20 and 21 at the upstream and downstream ends, respectively, of the valve body. Inner flat wall sections 19 are diametrically opposed to one another to extend between the wall sections 18 and, as shown in FIGS. 2 and 3, form a body of increased thickness with the external wall surface 16.

In order to control opening and closing movement of the occluder leaflets 14, each inner wall section 19 is formed with a pair of shallow guide pockets or cavities 24 and 25 recessed into each wall section 19. As viewed in FIG. 2, a pair of pockets 24 are aligned in opposite wall sections 19 to control opening and closing movement of the lefthand occluder leaflet, and a pair of pockets 25 are similarly aligned to control opening and closing movement of the righthand leaflet. A description of the pockets 24 and 25 illustrated in the sectional view of FIG. 1 will suffice for the pockets 24 and 25 on the opposite side of the body. Thus, each pocket 24 is disposed in closely-spaced, juxtaposed relation to a pocket 25, the pockets 24 and 25 being formed intermediately of each inner wall section 19 and symmetrically about a plane passing through the longitudinal axis of the body and through a point in the inner wall sections 19 intermediately between the pockets. Further each pocket 24 and 25 is correspondingly formed to be of open, generally polygonal or foursided configuration including an upstream edge 27 which inclines at an angle of approximately 45° to the longitudinal axis of the body so that the included angle between the sides 27 of pockets 24 and 25 is 90°. The upstream end of the side edge 27 terminates in a rounded corner edge 28 which is reverse-curved to extend into an inclined relatively straight, upstream edge 29 inclining at an approximate 45° angle to the longitudinal axis in a downstream direction away from the corner 28 and terminates in a rounded corner edge 30. Side edge 31 extends from the corner edge 30 at a very slight angle away from the axial direction, approximately 5°, and terminates in a downstream rounded corner 32. Downstream corner edge 32 is somewhat broader than the corner edges 28 and 30 and is reverse-curved to continue into a generally convex downstream edge 33 which slopes gradually in an upstream direction and terminates in an inner rounded corner 34. As illustrated in FIGS. 2 and 3, each pocket 24 and 25 is extremely shallow or of limited depth so as not to extend through the entire thickness of the inner wall section 18.

Preferably, the valve body 10 has a substrate 10' composed of a material, such as, graphite capable of withstanding elevated temperatures on the order of 1500° F. to 3000° C. and is covered by an outer layer of wear-resistant, high strength carbon material such as Pyrolite manufactured and sold by Carbomedics of San Diego, California. This material is inert in blood and has an EMF surface potential which will not attract the negatively charged blood cells.

The occluder valve elements or leaflets 14 are of corresponding size and configuration and are mounted within the valve body 10 so as to be disposed in confronting relation to one another symmetrically about the center or longitudinal axis of the valve body for movement between a closed position as shown in full and an open position as illustrated in dotted lines as shown in FIG. 1.

Considering in more detail FIGS. 1, 2, 4 and 5, each leaflet has a generally shovel or scoop-shaped major wall portion 40 of concavo-convex configuration so as to present an upstream concave surface 41 and a downstream surface 42. As viewed in the cross-sectional view of FIG. 5, the major wall portion 40 is of elliptical configuration, and opposite lateral edges of the wall terminate in straight-sided lateral edges or skirts 44 which project in an upstream direction and have laterally outwardly projecting slide control members 45 extending from the external surface of each skirt. As viewed in FIG. 4, each leaflet can be characterized as being in the form of a triangle having a hypotenuse formed along the external wall surface 42 and equilateral sides 47 and 48, the side 47 being formed by the leading or axially directed edge of the leaflet and the side 48 being formed by the trailing or radially directed edge of the leaflet. The triangle as described is somewhat truncated at the intersection of the sides 47 and 48 in the formation of the skirt portions 44 which extend at an angle to the longitudinal axis of the body corresponding to the angle of the side edge 27 of a pocket 24. Further, as illustrated in the plan view of FIG. 2, each trailing edge 48 is formed on a radius of curvature corresponding to that of the curved wall section 18 of the body and intersects the straight-sided skirts 44 at a point corresponding to the straight wall sections 19 of the body.

Each skirt 44 is provided with an elongated slide control member 45, the longitudinal axis of which extends parallel to the length of the skirts. Specifically in the arrangement as shown in FIG. 1, when the leaflets 14 are in their closed position as shown in full, each slide control member 45 will extend substantially at a 45° angle to the longitudinal axis of the body and parallel to the side edge 27 of each of the respective pockets. In addition, the slide control members 45 are of a length corresponding to the length of the side edges and in the closed position would extend along the side edges. Moreover, the external surface of each slide control surface is rounded both in a lengthwise direction as well as transversely so as to have generally spherical opposite ends, and the curvature of the slide control members correspond or are complementary to that of the respective pockets 24 and 25. Further, the slide control members are of a depth to be fully seated within each of the respective pockets with the lateral edges or skirts 44 disposed contiguous to the straight wall sections 19, for example, in the relationship as illustrated in FIG. 2.

When fluid under pressure is applied to the upstream sides of the leaflets 14, the opening pressure against the leaflets will be imparted to the slide control members 45 whereby to cause the slide control members to undergo both a translational and pivotal movement through the pockets 24 and 25. Specifically, the lower or upstream spherical end of a slide control member will be free to slide along the inclined edge 29 while the downstream spherical end of the slide control member will be free to undergo swinging movement as well as translational movement across the pocket between opposite side edges 27 and 31 until the slide control members reach a position in which the opposite side of the slide control member is flush with the side edge 31. At that point, the leaflets will have advanced to the open or dotted line position as illustrated in FIG. 1 and preferably such that they are disposed at a 5° angle to the longitudinal axis, or just less than parallel to the longitudinal axis. By virtue of the curvature of the leaflets, an open bore is provided between the leaflets for free passage of blood or other liquid and the bore formed is free of any obstructions other than the limited projection of the skirts along the straight wall sections. Most importantly however the main channel of flow centrally of the valve body is free of any obstruction whatsoever while avoiding any sockets or limited apertures which might otherwise tend to collect blood or other liquid. Moreover, the blood will be capable of passing between the skirt portions and straight wall sections so as to have the effect of a washing action on the mating surfaces between the skirts and straight wall sections as well as between the slide control members 45 and pockets 24 and 25. It will be noted that the radially outwardly inclined edge 29 is a relatively straight edge to permit controlled sliding movement of the member 45 therealong so that the movement of the leaflet in advancing from the closed to the open position is in a downstream and radially outward direction. The side edge 33, however, is given a slight concavity or curvature sufficient to afford clearance for swinging movement of the downstream edge of the control member 45 as it advances along the straight edge 29. Conversely, when the direction of fluid flow is reversed, the pressure against the convex or downstream surfaces as well as the leading edge surfaces of the leaflets will cause the slide control members 45 to undergo reverse movement in an upstream and radial inward direction until the leading edges 47 return to abutting relation to one another and the control members 45 engage the side edges 27. In the closed position as described, the trailing edges 48 are disposed in surface engagement with the inner walls 18.

DETAILED DESCRIPTION OF A MODIFIED EMBODIMENT

As illustrated in FIGS. 7 to 14, the modified form of the present invention is broadly made up of an annular valve body 50 surrounded by an outer concentric suture ring 12, the valve body 50 supporting a pair of occluder valve elements or leaflets 52. As illustrated, the suture ring 12 corresponds to that shown in the preferred form and includes an axially directed, circular wall portion 15 in outer concentric relation to the valve body 50. The wall portion 15 fits snugly within a channel-shaped external wall portion 54 of the valve body, and collar 17 projects from one end of the ring 12 on the upstream side of the valve for positioning of the entire assembly in place as described earlier.

The valve body 50 generally corresponds to the annular or generally circular configuration of the preferred form having inner circular wall surfaces 56 diametrically opposite to one another and separated by straight or flat wall sections 57. In cross-section wall surfaces 56 and 57 extend parallel to the central or longitudinal axis of the valve body and terminate in radially outwardly flared ends 59 and 60 at the upstream and downstream ends, respectively, of the valve body, the flared ends 59, 60 also merging into opposite ends of the channel-shaped wall section 54. A pair of nodes 62 are arranged in diametrically opposed relation to one another and project radially inwardly from the inner wall surface 56 of the valve body, the nodes each having a generally convex, axially extending inner wall surface 63 flanked by flat sidewall portions 64, as enumerated in FIGS. 9 and 10, each node defining a fulcrum about which an associated leaflet 52 is free to swing in advancing between an open and closed position. Additionally, pairs of radially inwardly directed projections or limit stops 67 and 68 are formed to extend inwardly from the valve body on opposite sides of each leaflet, each pair 67 and 68 being located adjacent to the point of divergency of the inner wall section 56 of the valve body into the upstream end 59 and being spaced intermediately between the nodes 62 but somewhat upstream thereof. Moreover, the wall sections 57 are each formed with a pair of guide lanes or channels 70 and 71 which are spaced somewhat inwardly and downstream of the respective limit stops 67 and 68 and are sloped so as to incline and diverge outwardly in a downstream direction away from one another. Each channel is correspondingly formed as a shallow, generally oval or cylindrical shaped depression recessed into the wall section 57 of the valve body including upstream rounded ends 69 of the channel pairs 70 and 71 being relatively near one another and downstream rounded ends 69' being located or spaced relatively away from one another. In this respect, it will be noted that each channel 70 and 71 inclines at an acute angle away from an imaginary axially directed plane passing intermediately between each channel of a pair, the angle or degree of inclination being dictated by the angle through which the leaflets are to pass in swinging between an open and closed position in a manner to be hereinafter described. In the modified form as shown, the channels extend at an approximate 45° angle to the imaginary plane as defined.

The occluder valve elements or leaflets are of corresponding size and configuration and therefore a description of one will suffice for both of the leaflets. Generally, the leaflets are disposed to be symmetrical about the center or longitudinal axis of the valve body so as to be movable between a closed position, as shown in full in FIG. 7, and an open position as illustrated in dotted lines. Considering in more detail FIGS. 8 and 12 to 14, each leaflet has a beveled leading edge 72, a rounded trailing edge 73 which is formed on a curvature corresponding to the radius of curvature of the inner wall section 57 of the valve body and lateral walls or skirts 74 which are flat and are formed on diametrically opposite sides of the valve body as described. Each of the skirts 74 forms an axially directed convergent extension in an upstream direction on opposite sides of the leaflets 52, and opposite edges of each skirt 74 form continuations of the trailing edge surface 73 and leading edge 72 of each leaflet.

In the modified form, each leaflet 52 is curved laterally across its entire width so as to be elliptical or of a progressively increased radius of curvature toward its center line, for example, as illustrated in FIG. 14. The leading edges 72 are curved along their length and in a plane which extends at an acute angle to the medial line passing along the length of each leaflet until it intersects the skirts 74. In turn, the skirts 74 incline generally in an upstream direction away from the leading edge surface 72 until they intersect the trailing edge surface 73. In this respect, the leaflets 52 correspond in configuration to the leaflets 14 of the preferred form.

Figure 7:
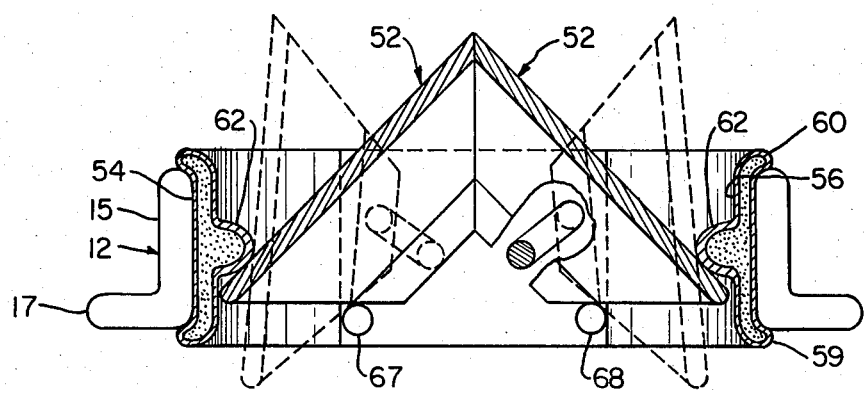
FIG. 7 is a cross-sectional view of a modified form of heart valve in accordance with the present invention.

In the modified form as illustrated, the leaflets are sized in relation to the valve body so as to extend at a substantially 45° angle inwardly toward the longitudinal axis of the valve when in the closed position. Accordingly, the leading edge surfaces 72 of the leaflets 52 are beveled to extend in a plane containing the longitudinal axis so that the beveled leading edge surface 72 of one leaflet will be flush with the leading edge surface 72 of the opposite leaflet when in the closed position. The skirts 74 in a plane parallel to the axially directed sidewalls 19 which contain the channels 70 and 71 and provide flat supporting surfaces for laterally projecting lugs or slide members 76 which extend toward the sidewall 19 for insertion into one of the guide channels 70 and 71. Each slide member 76 is in the form of a generally cylindrical protuberance which is sized to be of a diameter slightly less than the width of each respective channel 70 and 71 so as to freely advance between opposite end limits of the channel between a position as shown in full in the channel 70, as illustrated in FIG. 7, when the leaflets are in the closed position to the dotted line position designated at 76' when the leaflets are advanced to the fully open position, again as illustrated in FIG. 7.

In the assembly of the modified form of valve as described, each leaflet is inserted from the downstream side of the valve body and opposite skirts 52 of each leaflet are pressed together an amount necessary for the slide members 40 to clear the sidewalls 57 until they are aligned with their respective channels 70 and 71 and with the trailing edge surfaces 32 positioned upstream of the fulcrums 22.

The valve body is of a construction corresponding to that of the preferred form and is composed of the same materials. Similarly, the leaflets 52 are composed of the same material but will possess a slightly greater degree of resiliency than the valve body owing to the thinner cross-section of the leaflets and thus will possess a sufficient amount of resiliency to permit a slight degree of inward bending for insertion of the slide members 76 into the guide channels 70 and 71. In the closed position as shown in FIG. 1, the leaflets 52 are symmetrical about the longitudinal axis of the valve with the trailing edge surfaces 73 abutting the inner wall surfaces 56 and the lateral end walls 74 being contiguous to the straight wall sections 57 to effectively seal the valve against the reverse flow of liquid flowing in the upstream direction. However, under normal opening pressure of liquid flowing downstream against the inner surfaces of the leaflets, the leaflets will rapidly respond to the differential pressure to advance outwardly toward the opening position under the control of the slide members 76 advancing through the guide channels 70 and 71 and the rocking movement of the leaflets about the fulcrum surfaces 63. The guide channels 70 and 71 will limit opening movement of the leaflets to a position slightly less than an axial direction so that when the differential pressure is reversed and the pressure from the downstream side becomes greater than that on the upstream side, the pressure will be applied across the external surfaces of the leaflets in a direction to cause them to return to the closed position.

There is illustrated in FIG. 15 a modified pocket configuration 24' to be used in place of the pockets 24 of the preferred form as shown in FIGS. 1 to 6. Here the pocket 24' is of generally triangular configuration having relatively straight side edges 84 and 85 diverging away from a common, generally rounded corner 86 and merging into a generally convex side wall 87 which extends generally in an axial direction. Each pocket 24' is configured to receive a modified slide control member 45' which is positioned on the skirt portion 44 so as to have its length extending in a direction perpendicular to the longitudinal axis of the valve body when the leaflet is in a closed position. Accordingly, in the relationship shown in FIG. 15, the slide control member 45' is disposed along the upstream edge 85 of its associated pocket when the leaflet is in the closed position; and under opening pressure will pivot in a downstream direction about the rounded corner 86 until it moves into contact with the upstream edge 84.

Although the present invention has been described with particularity relative to the foregoing detailed description of the preferred embodiment, various modifications, changes, additions and applications other than those specifically mentioned herein will be readily apparent to those having normal skill in the art without departing from the spirit and scope of this invention.

I claim:

1. A prosthetic heart valve comprising:
an outer peripheral, generally annular body having an inner wall surface;
a pair of occluder leaflets disposed in said body, each including opposed lateral edge surfaces and leading and trailing edge surfaces; and
leaflet-supporting means operative to support said leaflets for movement in response to reversals in the direction of fluid flow through said body between an open position in which said leaflets are substantially parallel to one another within said body and a closed position in which said leaflets extend angularly across said body with said leading edges abutting one another, said leaflet-supporting means having lateral projections on opposed lateral edge surfaces elongated in a direction parallel to said lateral edge surfaces and guide pocket means for each of said lateral projections, each said guide pocket means being in the form of a shallow, multi-sided guide channel having opposite side edges divergent in a downstream direction, said lateral projections insertable in an associated channel and slidable through said channel between said opposite side edges, each pair of said guide channels on opposite sides of said leaflets formed symmetrically about a plane passing through the longitudinal axis of said valve body and intermediately between each channel of a pair, each channel having a generally convex downstream edge and an oppositely disposed, relatively straight upstream edge, said guide pocket means operative to guide pivotal and limited translatory movement of each said leaflet between said open and said closed positions in response to reversals in the direction of fluid flow through said body.

2. A prosthetic heart valve according to claim 1, said opposed lateral edge surfaces being flat and extending substantially parallel to one another and movable into substantially sealed relation with respect to a correspondingly flat inner wall surface portion of said body when said leaflets are advanced to the closed position.

3. A prosthetic heart valve according to claim 1, each leaflet having a pair of skirts extending substantially parallel to one another and to said flat inner wall surface portions of said body in a direction upstream of the direction of flow through said valve.

4. A prosthetic heart valve according to claim 1, said trailing edge surfaces of said leaflets being curved to conform to the inner wall surface of said body.

5. A prosthetic heart valve according to claim 1, said guide pocket means each being in the form of a shallow guide lane channel formed as a shallow depression in a flat inner wall surface portion of said body, said guide lane channel of each pair of guide lane channels on diametrically opposite sides of said body diverging away from one another at an acute angle from a point relatively near the leading edge surface of each respective leaflet.

6. A prosthetic heart valve comprising:
an outer peripheral body member having a generally circular inner wall surface interrupted by diametrically opposed flat wall sections;
a pair of occluder leaflets disposed in said body, each leaflet being of generally concavo-convex configuration to present a concave surface facing in a direction upstream of the flow of fluid therethrough and a convex surface facing in a direction downstream of the flow therethrough, lateral skirt portions on said leaflets extending substantially parallel to one another and to said flat wall sections from opposed lateral edge surfaces of each leaflet, a generally convex leading edge surface and a curved trailing edge surface wherein said leading edge surfaces are adapted to be movable into flush abutting relation to one another and said trailing edge surfaces are adapted to be movable into flush abutting relation to the inner wall surface of said body; and
leaflet support means between said skirt portions and said flat wall sections of said body operative to control movement of said leaflets between an open position in which the trailing edge surfaces of said leaflets are disposed substantially parallel to said generally circular inner wall surface of said body and a closed position in which said leaflets have their leading edge surfaces in flush abutting relation to one another, said leaflet supporting means having guide members projecting laterally in opposite directions from opposed skirt portions of each leaflet and guide channels disposed in said flat wall sections of said body adapted to receive said guide members to guide pivotal movement of each said respective leaflet between an open and a closed position.

7. A prosthetic heart valve according to claim 1, each said relatively straight upstream edge being shorter than said convex downstream edge and of a length greater than the width of said lateral projection, each of said lateral projections being free to undergo translational and pivotal movement in said channels in moving said occluder leaflets between the open and closed positions.

8. A prosthetic heart valve according to claim 6, said flat wall sections of said body being coextensive with said skirt portions on said leaflets.

9. A prosthetic heart valve according to claim 6, said flat wall sections provided with radial inward projections in the form of diametrically opposed fulcrums symmetrically located with respect to said leaflets intermediately between said guide means.

10. A prosthetic heart valve according to claim 9, said limit stops projecting inwardly from said flat wall sections of said body on the upstream side of said leaflets.

11. A prosthetic heart valve according to claim 6, each of said occluder leaflets being generally elliptical in cross-section.

12. A prosthetic heart valve according to claim 6, including limit stop members interposed between flat wall sections of said body and opposed lateral edge surfaces of said leaflets.

13. A prosthetic heart valve adapted for controlling the flow of blood in the heart of a mammal comprising:
an outer peripheral, generally annular body;
a pair of occluder leaflets disposed in said body, each including opposed lateral edge surfaces and leading and trailing edge surfaces, lateral skirt portions on said leaflets extending substantially parallel to one another and to said flat wall sections from opposed lateral edge surfaces of each leaflet, said lateral skirt portions movable into substantially sealed relation with respect to said flat wall sections of said body when said leaflets are advanced to the closed position; and leaflet-support means supporting said leaflets for movement between an open position in which said leaflets are substantially parallel to one another and a closed position in which said leaflets are oppositely inclined across said body with said leading edges abutting one another, said leaflet-supporting means having lateral generally oval-shaped projections on opposed lateral edge surfaces, each projection elongated in a direction parallel to said lateral edge surfaces and guide pocket means in said inner wall surface for each of said lateral projections, each said guide pocket means disposed in the inner wall surface of said body between said leading and trailing edge surface of a respective leaflet, each said guide pocket means aligned to receive a lateral projection whereby to guide each said leaflet to slide and pivot in moving between the closed and the open positions.

14. A prosthetic heart valve according to claim 13, each guide pocket means in cooperation with said associated lateral projection preventing axial shifting of said occluder leaflets between said open and closed positions.

15. A prosthetic heart valve according to claim 13, said lateral projections being externally rounded throughout their length and breadth, and each respective guide pocket means being in the form of a shallow recess having a curvature substantially complementary to that of each associated lateral projection.

16. A prosthetic heart valve according to claim 15, said guide pocket means each being formed as a shallow depression in the inner wall surface of said body, each pair of said guide pocket means on a diametrically opposite side of said body diverging away from one another at an acute angle to the longitudinal axis of said body.

17. A prosthetic heart valve according to claim 13, said leaflets each being of relatively thin, concavo-convex configuration provided with a concave surface facing in a direction upstream of the direction of flow through said valve and a convex surface facing in a direction downstream of the direction of flow of fluid through said valve.

* * * * *